(12) United States Patent
Clementi et al.

(10) Patent No.: US 8,256,453 B2
(45) Date of Patent: Sep. 4, 2012

(54) VACUUM REGULATOR HAVING SELECTABLE ADJUSTMENT RANGES

(75) Inventors: Francis J. Clementi, Somerset, PA (US); Joel David Neatrour, Johnstown, PA (US)

(73) Assignee: DeVilbiss Healthcare, LLC, Somerset, PA (US)

( * ) Notice: Subject to any disclaimer, the term of this patent is extended or adjusted under 35 U.S.C. 154(b) by 1027 days.

(21) Appl. No.: 12/150,776

(22) Filed: May 1, 2008

(65) Prior Publication Data

US 2009/0272444 A1 Nov. 5, 2009

(51) Int. Cl.
*F16K 17/00* (2006.01)
(52) U.S. Cl. .......... 137/526; 137/530; 137/540
(58) Field of Classification Search ........ 137/526, 137/528, 529, 530, 535, 565.26, 538, 540
See application file for complete search history.

(56) References Cited

U.S. PATENT DOCUMENTS

| | | | | |
|---|---|---|---|---|
| 1,164,098 | A * | 12/1915 | Kinsey, Jr. ............... | 137/526 |
| 2,735,669 | A * | 2/1956 | Seiler ..................... | 267/175 |
| 3,013,790 | A * | 12/1961 | Anderson et al. ......... | 267/175 |
| 3,963,027 | A | 6/1976 | Muriot | |
| 4,228,798 | A | 10/1980 | Deaton | |
| 4,468,226 | A | 8/1984 | Kurtz et al. | |
| 4,485,843 | A * | 12/1984 | Wolff ..................... | 137/514 |
| 4,487,606 | A | 12/1984 | Leviton et al. | |
| 4,497,300 | A | 2/1985 | Maruyama et al. | |
| 4,545,405 | A * | 10/1985 | LaBelle ................... | 137/524 |
| 4,679,466 | A | 7/1987 | Kumura et al. | |
| 4,698,060 | A | 10/1987 | D'Antonio et al. | |
| 4,777,978 | A * | 10/1988 | Hsiao ...................... | 137/524 |
| 4,915,691 | A | 4/1990 | Jones et al. | |
| 4,930,997 | A | 6/1990 | Bennett | |
| 4,941,503 | A * | 7/1990 | Hubner, Jr. .............. | 137/454.2 |
| 5,156,602 | A | 10/1992 | Steffler | |
| 5,195,961 | A | 3/1993 | Takahashi et al. | |
| 5,300,050 | A | 4/1994 | Everett, Jr. et al. | |
| 5,466,229 | A | 11/1995 | Elson et al. | |
| 5,589,145 | A | 12/1996 | Kaufman | |
| 5,620,428 | A | 4/1997 | Hand | |
| 5,669,892 | A | 9/1997 | Keogh et al. | |
| 5,682,624 | A * | 11/1997 | Ciochetti ................ | 4/509 |
| 5,691,753 | A | 11/1997 | Hilton | |
| 5,807,359 | A | 9/1998 | Bemis et al. | |
| 5,878,663 | A | 3/1999 | Krzyzak et al. | |
| 5,931,822 | A | 8/1999 | Bemis et al. | |
| 5,950,623 | A * | 9/1999 | Michell ................... | 128/205.24 |
| 5,960,823 | A * | 10/1999 | Wilkins .................. | 137/516.25 |
| 6,189,531 | B1 * | 2/2001 | Tatarek ................... | 128/205.24 |
| 6,244,311 | B1 | 6/2001 | Hand et al. | |
| 6,358,218 | B1 | 3/2002 | Want et al. | |
| 6,358,232 | B1 | 3/2002 | Hand et al. | |
| 6,368,310 | B1 | 4/2002 | Bemis et al. | |
| 6,368,311 | B1 | 4/2002 | Valerio et al. | |

(Continued)

*Primary Examiner* — Craig Schneider
*Assistant Examiner* — David Colon Morales
(74) *Attorney, Agent, or Firm* — Fox Rothschild LLP; Dennis M. Carleton

(57) ABSTRACT

A vacuum regulator has a vacuum range controller and a manifold including an inlet opening, a vacuum source connection, and a bleed orifice. The vacuum range controller includes a regulator stem having a metering tip, a stem body, and an adjustment rod. The metering tip is selectively positioned against the bleed orifice. The vacuum range controller further includes a vacuum adjuster having an adjustment collar and a resilient member which are coaxially disposed on a portion of the regulator stem. An adjustment knob engages the adjustment rod for concurrent rotational movement therewith.

7 Claims, 3 Drawing Sheets

U.S. PATENT DOCUMENTS

| | | |
|---|---|---|
| 6,447,473 B1 | 9/2002 | Levine et al. |
| 6,494,869 B1 | 12/2002 | Hand et al. |
| 6,623,463 B2 * | 9/2003 | Jones et al. .................. 604/319 |
| 6,644,313 B2 * | 11/2003 | Prime et al. .............. 128/205.24 |
| 6,673,055 B2 | 1/2004 | Bemis et al. |
| 6,691,735 B1 * | 2/2004 | Harneit ........................ 137/524 |
| 6,955,664 B2 | 10/2005 | D'Antonio |
| 6,959,722 B2 * | 11/2005 | Fontanili et al. .............. 137/205 |
| 7,115,115 B2 | 10/2006 | Bemis et al. |
| 7,153,294 B1 | 12/2006 | Farrow |
| 7,175,612 B2 | 2/2007 | Felix et al. |

\* cited by examiner

VACUUM REGULATOR HAVING SELECTABLE ADJUSTMENT RANGES

TECHNICAL FIELD

This invention relates in general to vacuum regulators. More specifically, the invention is directed to vacuum regulators for use with medical suction and aspirator devices.

BACKGROUND OF THE INVENTION

Medical suction and aspiration devices are used to remove bodily fluids during medical procedures or emergency situations. These suction and aspiration devices often require adjustment of the vacuum level applied to a patient. It is desirable to allow an operator to control the vacuum applied to a suction tool during a procedure. The invention provides a vacuum regulator having a plurality of vacuum adjustment ranges. The vacuum adjustment ranges each includes an adjustment capability within the limits of a selected vacuum adjustment range.

BRIEF SUMMARY OF THE INVENTION

This invention is a vacuum regulator having a manifold including an inlet opening, a vacuum source connection, and a bleed orifice. A regulator stem has a metering tip, a stem body, and an adjustment rod. The metering tip is selectively positioned against the bleed orifice. A vacuum adjuster has an adjustment collar and a resilient member that are coaxially disposed on a portion of the regulator stem. An adjustment knob engages the adjustment rod for concurrent rotational movement therewith.

DESCRIPTION OF THE INVENTION

Figure 1:
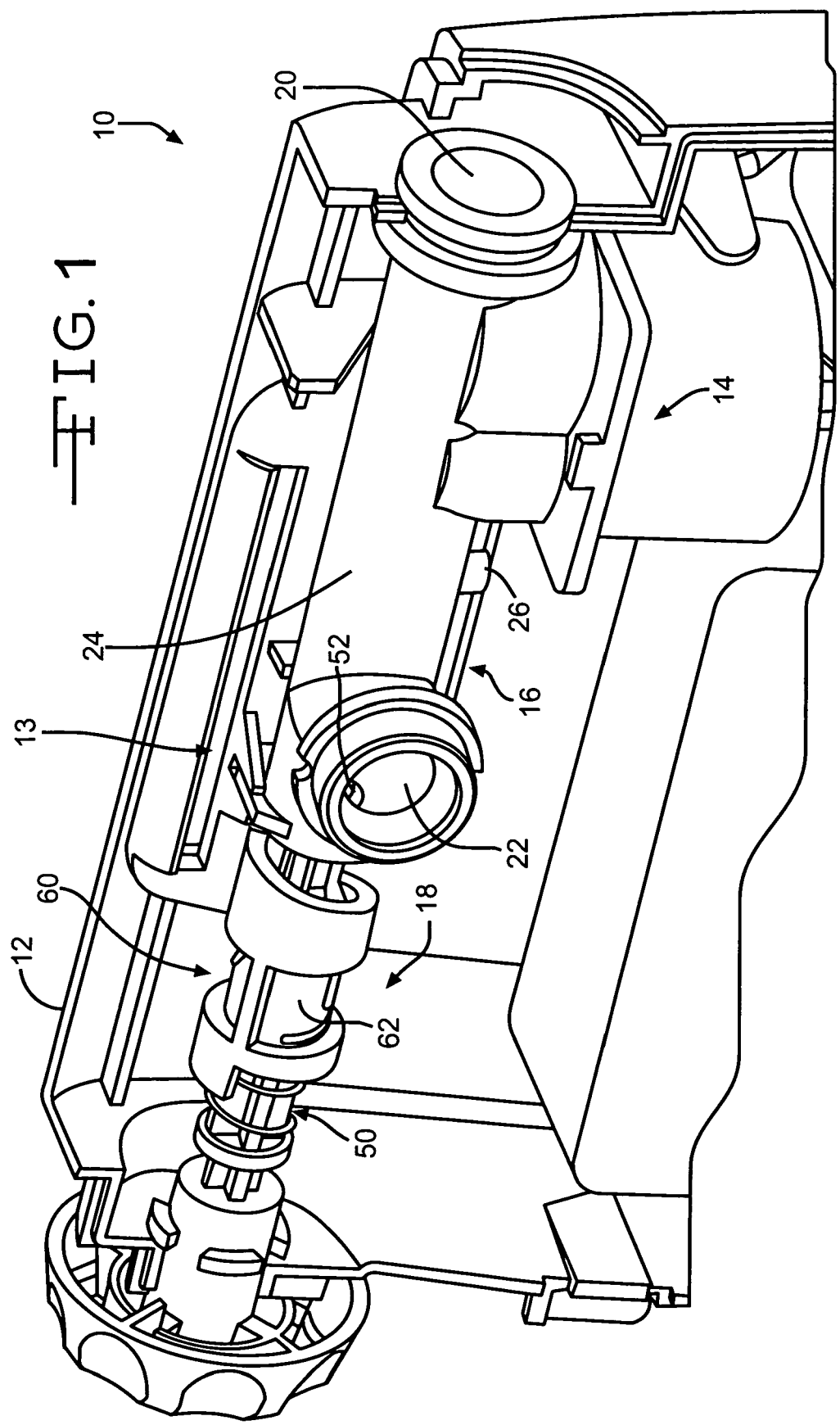
FIG. 1 is a front perspective view of a vacuum regulator according to the invention.

Referring now to the drawings, a suction device 10 having a housing 12 is shown in FIG. 1. The housing 12 is approximately one half of a complete housing structure where the other housing portion (not shown) is generally the complimentary or mirror image of the housing 12. The two housing halves cooperate to orient and enclose the various components of the suction device 10. The housing 12 may be formed in one piece or from a plurality of pieces if so desired. The housing 12 provides relative positioning and fixturing of a vacuum regulator 13 that includes a vacuum manifold, shown generally at 16, and a vacuum range controller, shown generally at 18. The housing can also position and secure a suction pump, shown generally at 14.

Figure 2:
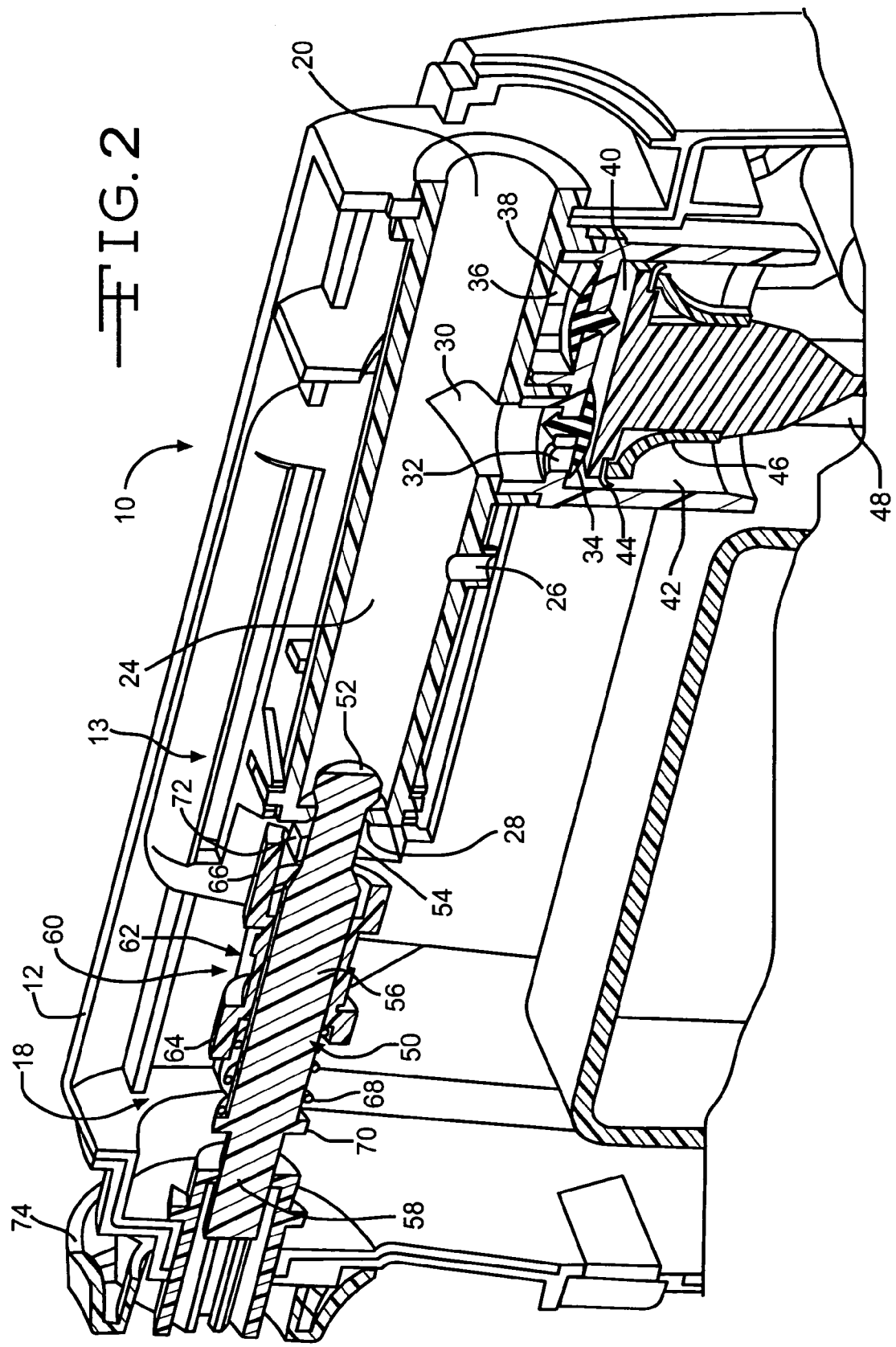
FIG. 2 is a view similar to FIG. 1 showing the vacuum regulator in cross section.

Referring to FIGS. 1 and 2, the vacuum manifold 16 includes a first inlet opening 20 and a second inlet opening 22. The first and second inlet openings 20 and 22 communicate through a manifold regulator tube 24 with the suction pump 14, a vacuum monitoring port 26, and a bleed orifice 28. In an embodiment of the invention, either the first or second inlet opening is functional and the other opening is closed.

As shown in FIG. 2, a vacuum pump intake 30 provides a negative pressure communication between the suction pump 14 and one of the first and second inlet openings 20 and 22. The strength of the negative pressure drawn in by, for example, the inlet opening 20 is adjusted and controlled by the vacuum regulator 13. An intake orifice 32 is coupled with the intake 30 for selective fluid communication by an intake valve 34. The intake orifice 32 may be a singular aperture or a plurality of apertures. The intake valve 34 is shown having a reed-type valve configuration, but any valve arrangement that can operate from a closed position to an open position to allow a generally one-way fluid communication between the suction pump 14 and the intake 30 may be used.

Still referring to FIG. 2, an exhaust port 36 is selectively coupled for fluid communication with a cooperating piston 40 and a cylinder 42 by an exhaust valve 38. The exhaust valve 38 is shown having a reed-type valve configuration, but any valve arrangement that can operate from a closed position to an open position to allow substantially one-way fluid communication between the piston 40 and the exhaust port 36 may be used. The piston 40 and the cylinder 42 provide a variable volumetric cavity that draws in and expels a fluid, such as air. The piston 40 includes a seal 44 and a seal support 46 that cooperate to provide a sliding seal engagement against the inner surface of the cylinder 42. The piston 40 is coupled to a motor (not shown) and a crank mechanism (not shown) by a connecting rod 48. Though shown as a singular structure, the piston 40 and rod 48 may be separate structures, either rigidly, pivotally, or flexibly engaged together. Alternatively, the vacuum pump 14 may be a separate unit located outside of the housing 12.

Figure 3:
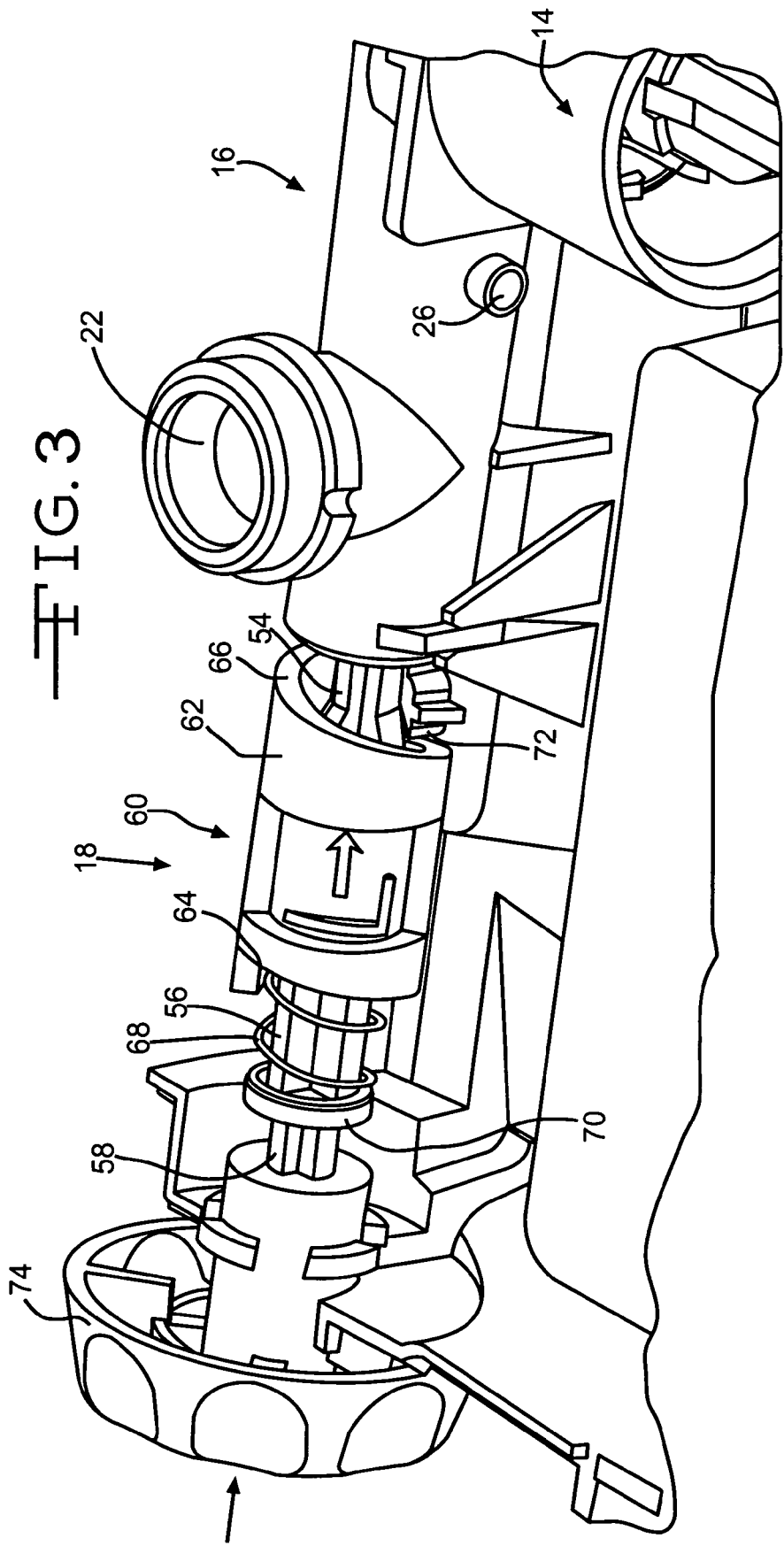
FIG. 3 is a bottom perspective view of the vacuum regulator shown in FIG. 1.

Referring to FIGS. 2 and 3, the vacuum range controller 18 of the vacuum regulator 13 includes a regulator stem 50 having a metering tip 52, a necked-down portion 54, a stem body 56, and an adjustment rod 58. The metering tip 52 is disposed within a portion of the manifold 16 and includes the necked-down portion 54 extending through the bleed orifice 28. The metering tip 52 is movable relative to the bleed orifice 28 to create a variable orifice size and thus a variable fluid flow or negative pressure characteristic at the selected first and second inlet opening 20 and 22. The stem body 56 extends from the necked-down portion 54 and terminates in the adjustment rod 58. The stem body 56 and the adjustment rod 58 have torque-transmitting outer profiles that also accommodate relative linear movement of a mating component engaged thereon. The torque-transmitting profile is shown as crossed axis projections, though any suitable geometry may be used, such as for example, triangular, square, hexagonal, and oval geometries.

Still referring to FIGS. 2 and 3, the vacuum range controller 18 further includes a vacuum adjuster 60 that includes an adjustment collar 62 having a first helix 64 and a second helix 66, and a resilient member 68. The outer profile of the stem body 56 engages a correspondingly shaped bore formed through the adjustment collar 62. The adjustment collar 62 is supported by the stem body 56 for relative linear movement and concurrent rotation therewith. The first helix 64 defines a first vacuum adjustment range and the second helix defines a second vacuum adjustment range. One of the first and second vacuum adjustment ranges is greater than the other adjustment range. The resilient member 68 is shown disposed coaxially onto the stem body 56, but other orientations may be used. The resilient member 68 provides a biasing force that reacts between the adjustment collar 62 and a resilient member stop 70. The resilient member stop 70 is positioned between the stem body 56 and the adjustment rod 58 of the regulator stem 50. Depending upon the desired range of vacuum operation intended for the suction device 10, the selected one of the first and second helixes 64 and 66 locates against a helix seat 72 to provide the vacuum adjustment range associated therewith.

The suction device 10, including the housing 12, the vacuum manifold 16, and the vacuum range controller 18 may be made from any variety of materials suitable to such devices. These materials may be plastics, such as polyethylene, polyvinyl chloride, polyetheretherketone (PEEK), polystyrene, polypropylene, polycarbonate, or other suitable plastic materials. Alternatively, some or all of the components may be made from metals, such as aluminum, stainless steel, brass, copper, or sintered alloys of these metals, in combination with various other alloying constituents.

In operation, the regulator 13 maintains the vacuum level in the manifold 16 by admitting a fluid at a positive pressure that is greater than the vacuum source negative pressure, such as air at ambient pressure through the bleed orifice 28. The vacuum monitoring port 26 may be connected to a pressure transducer (not shown), controller (not shown), printed circuit board (not shown) or other display, control, or monitoring device. The monitoring port 26 provides a negative pressure signal for monitoring, controlling, or otherwise alerting a user to the operating condition of the device. The resilient member 68 of the vacuum range controller 18 establishes a threshold force required to move the metering tip 52 from engagement with the bleed orifice 28. An adjustment knob 74 engages the adjustment rod 58 for concurrent rotational movement therewith and relative sliding linear movement therebetween.

Referring to FIG. 3, as the adjustment knob 74 is rotated, for example in a clockwise direction as viewed in the direction of the arrow, the adjustment rod 58, stem body 56, metering tip 52, and adjustment collar 62 rotate therewith. The selected helix, such as the second helix 66, which is located against the helix seat 72 by the biasing force of the resilient member 68, moves relative to the helix seat 72 as the adjustment knob 74 is rotated. As the second helix 66 moves against the helix seat 72, the adjustment collar 62 is displaced linearly toward the resilient member stop 70 thus compressing the resilient member 68 contained therebetween. As the resilient member 68 is compressed between the collar 62 and the stop 70, a greater force is exerted by the metering tip 52 onto the bleed orifice 28, thus increasing the resistance to unseat the tip 52 from the orifice 28.

This greater unseating force of the metering tip 52 thus requires a stronger vacuum response force to overcome the biasing force keeping the bleed orifice 28 blocked. Once a sufficient vacuum level is generated in the manifold regulator tube 24 to overcome the biasing force, the metering tip 52 lifts off of the bleed orifice 28 and air is drawn into the manifold regulator tube 24. Further, the adjustment rod 58 is also free to move axially relative to the adjustment knob 74 in response to the vacuum level. The air, admitted at ambient pressure, mitigates the negative pressure created by the suction pump 14 at the selected one of the first and second inlet openings 20 and 22.

While the invention has been described with reference to particular embodiments, it should be understood that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiments, but that the invention shall include all embodiments falling within the scope of the claims.

What is claimed is:

1. A vacuum regulator comprising:
   a manifold having an inlet opening, a vacuum source connection and a bleed orifice;
   a regulator stem having a metering tip, a stem body and an adjustment rod, the metering tip being selectively positioned against the bleed orifice, said stem body having a necked-down portion adjacent said metering tip which extends through said bleed orifice;
   a resilient member stop defined on said regulator stem;
   a stationary helix seat;
   a vacuum adjuster having a helix defined at one end thereof engaging said helix seat and an adjustment collar defined in the opposite end thereof, the vacuum adjuster being coaxially disposed on a portion of the regulator stem;
   a resilient member engaging said resilient member stop defined on said regulator stem and said adjustment collar defined on said vacuum adjuster; and
   an adjustment knob engaging the adjustment rod for concurrent rotational movement therewith;
   wherein said stem body defines a torque-transmitting outer profile and further wherein said vacuum adjuster defines a mating bore such that rotational movement of said stem body causes concurrent rotational motion of said vacuum adjuster and linear motion of said vacuum adjuster relative to said stem body as said helix rotates against said stationary helix seat;
   and further wherein said linear motion of said vacuum adjuster relative to said stem body varies the compression of said resilient member, thereby varying the vacuum force required to move said metering tip away from said bleed orifice.

2. The vacuum regulator of claim 1, wherein the bleed orifice is in fluid communication with an atmospheric pressure source.

3. The vacuum regulator of claim 2 wherein the metering tip seats against a portion of the bleed orifice and moves relative to the bleed orifice to vary the fluid flow therethrough in response to the vacuum adjuster.

4. The vacuum regulator of claim 1 wherein the metering tip moves relative to the bleed orifice in response to a vacuum induced force working against a force generated by the resilient member.

5. The vacuum regulator of claim 1 wherein the resilient member is compressed and expanded by the relative linear movement of the vacuum adjuster along the stem body.

6. The vacuum regulator of claim 1 wherein the resilient member is a coil spring.

7. The vacuum regulator of claim 1 wherein the resilient member is coaxially disposed on a portion of the regulator stem.

* * * * *